United States Patent [19]

Shirakawa

[11] Plant 5,083

[45] Aug. 9, 1983

[54] HYBRID TEA ROSE NAMED YOKO

[75] Inventor: Takeshi Shirakawa, Gamagori, Japan

[73] Assignee: Toshio Nakashima, San Leandro, Calif.

[21] Appl. No.: 370,611

[22] Filed: Apr. 22, 1982

[51] Int. Cl.[3] ..... A01H 5/00

[52] U.S. Cl. ..... Plt./20

[58] Field of Search ..... Plt./20

*Primary Examiner*—Robert E. Bagwill

*Attorney, Agent, or Firm*—Chas. W. Rummler

[57] ABSTRACT

A new variety of hybrid tea rose intended mainly for greenhouse culture and the commercial production of cut flowers, characterized by a continuous and profuse production of very large red blooms carried on very long, strong stems; its pointed and somewhat globular buds which open slowly to produce well formed flowers having large petals which tend to marginally turn under and form points; its free branching and vigorous growth habit; and its abundant production of foliage and long lasting vase life.

3 Drawing Figures

BACKGROUND OF THE NEW PLANT

My new variety of rose plant is the result of breeding efforts carried on by me at 20 Koyama, Takenoya-cho, Gamagori-shi, Aichi Ken, Japan, with the object of producing an orange-red rose having an upright growth habit with very long stems and an excellent vase life with no tendency to blue in the fully opened bloom. This plant originated as a seedling derived by my crossing of an unnamed seedling with the variety "Prominent" (U.S. Plant Pat. No. 3,380), the unnamed seed parent having resulted from the cross of an unnamed seedling by "Happiness" (U.S. Plant Pat. No. 911), in my greenhouse breeding facilities in Japan. The form and beauty of the flowers of this new plant and its very fine growth habit led me to propagate this plant through several generations, by budding, which showed that the novel characteristics of this plant would hold true from generation to generation and as a result, commercial propagation of this plant, by budding, is now being carried on under my direction in Japan.

DESCRIPTION OF THE DRAWINGS

My new variety of rose plant is illustrated by the accompanying photographic drawings, sheet one of which shows a fully opened flower together with some foliage; sheet two shows several stages of bud opening from the time when the calyx breaks; and sheet three shows the upper and under side views of typical leaves together with specimens of young and old wood, and a bud in the first of its opening stages. The flower colors shown in the drawings are as nearly true as can be obtained by careful conventional photographic procedures.

DESCRIPTION OF THE NEW PLANT

The following is a detailed description of my new rose plant with color designations according to The R.H.S. Colour Chart published by The Royal Horticultural Society of London, England.

THE PLANT

Origin: Seedling.

Parentage:

*Seed parent.*—An unnamed seedling derived from the crossing of another unnamed seedling with "Hapiness" (U.S. Plant Pat. No. 911).

*Pollen parent.*—"Prominent" (U.S. Plant Pat. No. 3,380).

Classification:

*Botanic.*—Hybrid Tea.

*Commercial.*—Greenhouse rose.

Form: Bush.

Habit: Upright and much branched.

Growth: Free and vigorous.

Height: About 5 feet.

Canes: Very strong, sturdy and upright.

Foliage:

*Quantity.*—Abundant.

*Number of leaves.*—5 to 6 on cut flower stems spaced 1¾ to 2½ inches apart.

*Shape of leaf.*—Pinnate.

*Leaflets.*—Shape: Ovate with acute apex and serrated margins. Size: About 4½ inches to 6 inches long and about 3¼ inches wide. Number: 3 to 7. Texture: Leathery. Aspect: Glossy. Color: Upper side — Yellow Green 147A. Under side — Yellow Green 148C. Petioles: ½ inch long by 1/12 inch wide. Petiolue: 1/32 inch long by 1/32 inch wide. Ribs and veins: Prominent; slightly depressed on upper side and more prominent on under side.

Thorns:

*Size.*—About 3/16 to ¼ inch long and ⅛ inch to ¼ inch wide. Most are hooked slightly downward.

*Color.*—48B at base to Greyed Orange 163B at tip.

THE BUD

Form: Pointed.

Size: 1¼ inch to 1½ inch long and 1 inch to 1¼ inch in diameter at center of bud.

Color:

*When sepals first divide.*—Orange Red 33A.

*When petals begin to unfurl.*—Red 40A.

Sepals: The sepals stand up initially and as the flower opens the sepals curl back and fold down parallel with the stem.

*Shape.*—Usually 2 are foliaceous and 2 are ovate.

*Color.*—Inside: Foliaceous sepals — Yellow Green 147A. Ovate sepals — Yellow Green 144B. Outside: Foliaceous sepals — Yellow Green 148B. Ovate sepals — Yellow Green 144B.

Calyx:

*Shape.*—Globular but depressed at top.

*Size.*—Small; about ⅜ inch wide and ⅜ inch long.

*Aspect.*—Smooth.

Peduncle:

*Length.*—About 3½ inches to 5 inches.

*Strength.*—Erect, holding flower upright.

*Color.*—On side facing sunlight — Yellow Green 146B. On shady side — Yellow Green 146C.

THE FLOWER

Blooming habit: Continuous and abundant.

Borne: Singly on strong stems.

Size: Very large; about 4¼ to 5 inches in diameter and about 1½ inches deep.

Shape:

*When bloom first opens.*—Flat.

*As bloom matures.*—It becomes open centered.

Petalage:

*Number of petals.*—30 to 35.

*Arrangement.*—Imbricated.

*Form.*—Outside and intermediate petals are obovate with entire margins which tend to turn under and form points at petal apex.

*Texture.*—Leathery.

*Appearance.*—Velvety.

*Color.*—Outer petals: Top side — Red Group 40A to 41A. At base — Yellow Green Group 154D. Reverse side: Margin — Red Group 46D. Center — Red Group 45D. Base — Yellow Group 2D. Inside petals: Face side: Margin — Red Group 43A. Base — Yellow Group 7C. Reverse side: Margin — Red Group 45C. Center — Red Group 45C. Base — Yellow Group 8C.

Petaloids:

*Number.*—1 to 3.

*Size.*—About ½ inch to ¾ inch long and ⅜ to ⅝ inch wide.

*Color.*—Red 40B with Yellow 2C at base.

Peduncle:

*Length.*—4½ to 5 inches.

*Character.*—Sturdy and upright.

*Color.*—Yellow Green 146B.

Persistence: Petals stay on stem 18 to 20 days and drop cleanly.

Fragrance: A sweet musk odor.

Lasting quality:

*On plant.*—18 to 20 days.

*As cut flower.*—14 to 18 days.

REPRODUCTIVE ORGANS

Stamens:

*Anthers.*—Number: 80 to 110. Length: 1/12 to ⅛ inch. Arrangement: Introse. Color: Yellow Orange 17B.

*Filaments.*—Length: ¼ inch. Color: Near anther — Yellow 2B. At base — Yellow 3C. Center — 41C.

*Pollen.*—Color — Greyed Orange 163B.

Pistils:

*Styles.*—Number: 55 to 80. Length: ½ inch to ⅝ inch.

*Stigmas.*—Color — Yellow 162B.

*Ovaries.*—Very slender and covered with silvery white hairs.

This new variety of rose plant has the growth habit of "Bettina" (unpatented) with the color of "Prominent" (U.S. Plant Pat. No. 3,380) but with very long stems and an excellent vase life.

I claim:

1. A new and distinct rose plant, substantially as herein shown and described, characterized by the brilliant red color of its very large flowers which are borne on long, strong stems, and its year around abundant production of blooms on long, strong stems.

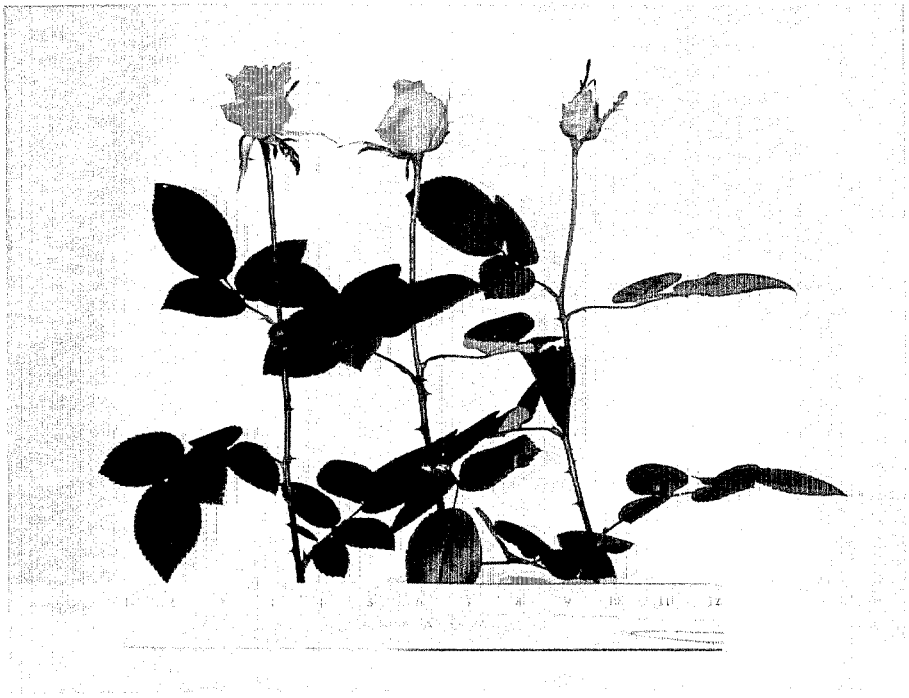
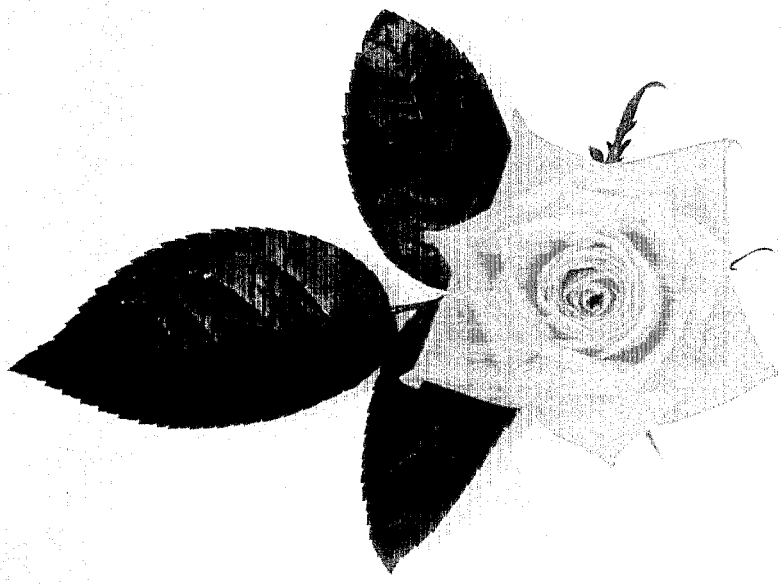

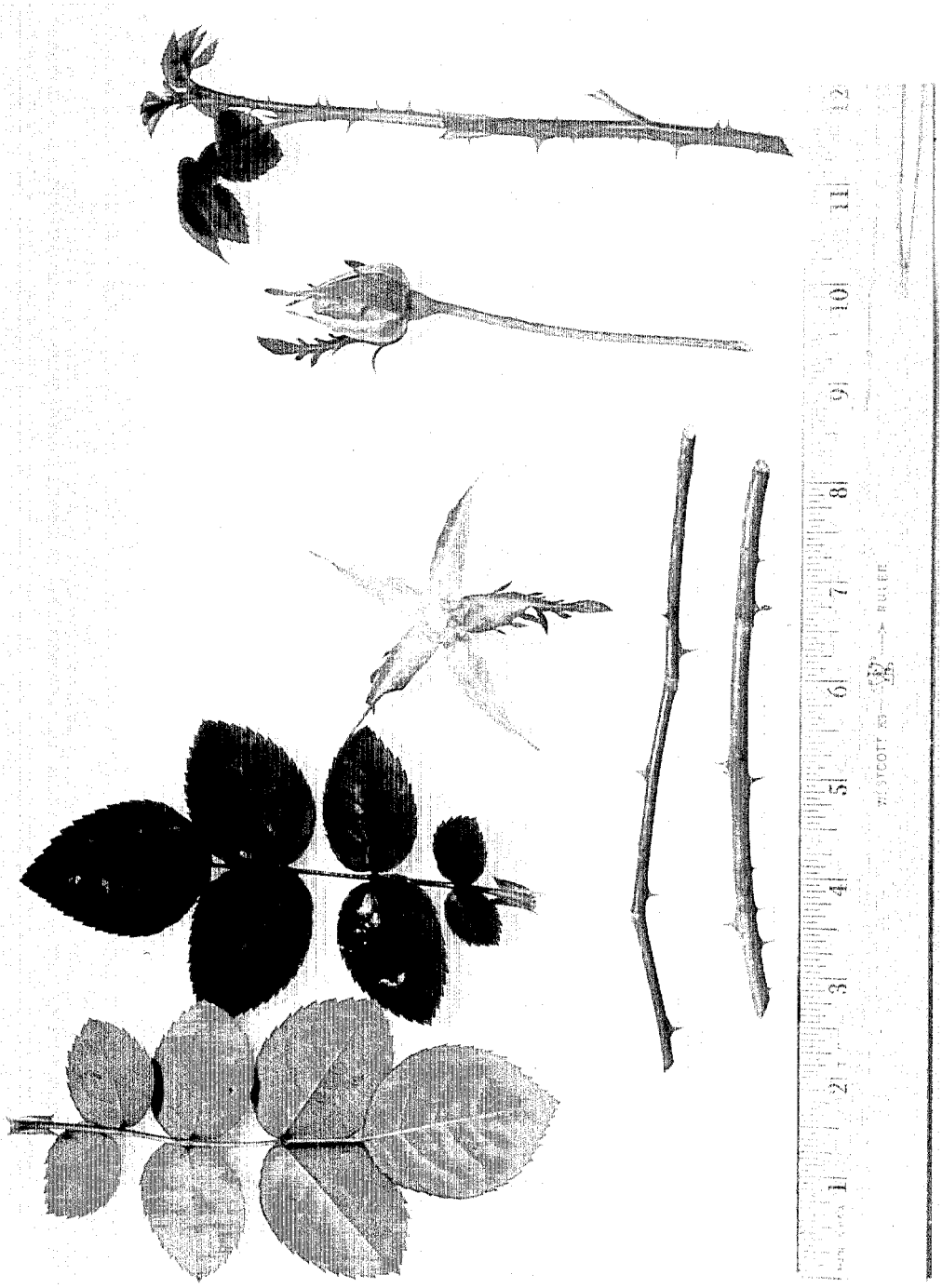

* * * * *